United States Patent [19]
Gianotti

[11] Patent Number: 5,836,962
[45] Date of Patent: Nov. 17, 1998

[54] ENDOPROSTHESIS

[75] Inventor: Marc Gianotti, Wiesendangen, Switzerland

[73] Assignee: Schneider (Europe) AG, Bulach, Switzerland

[21] Appl. No.: 787,817

[22] Filed: Jan. 22, 1997

Related U.S. Application Data

[63] Continuation of Ser. No. 326,630, Oct. 20, 1994, abandoned.

[30] Foreign Application Priority Data

Oct. 20, 1993 [EP] European Pat. Off. ............. 93116918

[51] Int. Cl.⁶ .......................... A61M 29/00; A61F 02/06
[52] U.S. Cl. ............................... 606/191; 606/198; 623/1
[58] Field of Search ................... 606/108, 151, 606/228, 232, 191, 200; 623/1, 11, 12; 428/373

[56] References Cited

U.S. PATENT DOCUMENTS

| | | | |
|---|---|---|---|
| 3,847,156 | 11/1974 | Trumble | 606/231 |
| 4,024,871 | 5/1977 | Stephenson | 606/231 |
| 4,655,771 | 4/1987 | Wallsten | 623/1 |
| 4,717,341 | 1/1988 | Goldberg et al. | 428/373 |
| 5,015,253 | 5/1991 | MacGregor | 623/1 |

FOREIGN PATENT DOCUMENTS

| | | |
|---|---|---|
| 441516A3 | 8/1991 | European Pat. Off. . |
| 556940A1 | 8/1993 | European Pat. Off. . |
| 91/12779 | 9/1991 | WIPO . |

OTHER PUBLICATIONS

European Search Report in corresponding European Application EP 93116918.9, together with Communiation dated Apr. 18, 1994 and one–page Annex.

*Primary Examiner*—Glenn K. Dawson
*Attorney, Agent, or Firm*—Peter C. Richardson; Lawrence C. Akers; Philip C. Strassburger

[57] ABSTRACT

A body compatible device including an elongate filament substantially uniform in lateral cross-section over its length and having multiple fibers having high tensile strength embedded in a polymeric material. The polymeric material may be melted onto the fibers, and the filament may have an elongate polymeric case surrounding the filament. The body compatible device may be a stent of a tubular latticework.

22 Claims, 2 Drawing Sheets

1

1

1 ns
ENDOPROTHESIS

This is a continuation, of application Ser. No. 08/326,630, filed on Oct. 20, 1994, now abandoned.

BACKGROUND OF THE INVENTION

The invention relates to an endoprosthesis for use in vessels of the human or animal body, and to a process for the fabrication thereof. Such endoprostheses are used in medicine when there is a risk of vascular occlusions primarily in blood vessels. They are taken, for example, percutaneously by means of a catheter to a site threatened by occlusion in an artery and anchored there temporarily or permanently, in that they expand elastically after removal of a shell or can be opened from outside by a force. They can also be used, however, in other vessels such as bronchi.

Endoprostheses are known, for example, from U.S. Pat. No. 4,655,771. The endoprostheses described therein consist of two interwoven groups, running in opposite directions, of wires, bent in a helical line, twisted against each other, and made of elastic stainless steel. Such endoprostheses are highly compressible in cross section and therefore can be easily inserted. Steel wires are also stiff enough to assure automatic expansion of the endoprosthesis after insertion. In the above-mentioned patent, the possibility is also mentioned of using filaments made of plastic or composite material, whereby however the latter concept is not further explained.

Filaments made of steel have major disadvantages. They are not ideally biocompatible and the ends of the steel filaments in the endoprosthesis tissue must be specially treated so that they do not trigger turbulences in the blood stream and do not act thrombogenically. It is therefore not possible to fabricate endoprostheses in a standard length and to cut them to a suitable length only immediately before use. They must be fabricated in several lengths and stored.

Filaments made of plastic are indeed more favorable, relative to their biocompatibility, and also better cuttable, perhaps with water-jet cutters; on the other hand, they often do not have the necessary stiffness or they must be relatively thick to achieve the said stiffness, so that the endoprosthesis is less compressible and therefore more difficult to insert than one constructed from steel wires.

Filaments made from composite materials can combine the positive properties of steel filaments with those of plastic filaments. This advantage alone, however, was not exceptional enough thus far to popularize the use of filaments made from composite materials in endoprostheses.

SUMMARY OF THE INVENTION

The invention has as its object the provision of an endoprosthesis of the aforementioned type with filaments made of composite material, which combine high biocompatibility and good cuttability with favorable mechanical properties, in particular, a small filament diameter and enough flexural rigidity of the filament to achieve sufficient resilience, but at the same time the course of a treatment with the endoprosthesis is to be improved by the new endoprosthesis in regard to the necessary operations, reliability and safety, patient stress, and the chances of success. In addition, a suitable process for the fabrication of such endoprostheses is to be specified.

This object is attained by means of the invention as it is characterized in the claims.

Broadly, the present invention relates to an endoprosthesis for use in vessels of the human or animal body, with a tubular latticework made of rigid elastic filaments made of a composite material, whereby the composite material is composed of several elements with a high tensile strength in each case, which to achieve a high flexural rigidity of the filament are sheathed by a support with a low tensile strength, characterized by a special preparation of the constituents, which further broadens the function of the support substance during the use of the endoprosthesis in the human or animal body through the contribution of these support materials to the flexural rigidity of the filaments. The special preparation of the carrier material may consist of a sized shell, surrounding the filament, which is indissolubly anchored in the filament surface of the support, the said shell which does not substantially alter the tensile strength of the filament. Both the support and also the material of the shell may each contain a thermoplastic, and the thermoplastic of the support may be melted onto the filament surface and melted together with the thermoplastic of the shell material. The shell may contain the same thermoplastic as the support. The support or the shell materials may be prepared from a mixture of substances, which contains a contrast medium. The material located on the filament exterior may be prepared from a mixture of substances, which contains a medication effective in the human or animal body. The special preparation of the support may consist of the material located on the filament exterior upon transition to its solid phase forming an especially large surface on which a coating of the filament is anchored. The special preparation of the support may consist of the material located on the filament exterior forming pores in which a medication effective in the human or animal body is stored.

The present invention also relates to a process for the fabrication of an endoprosthesis wherein the fabrication of a filament support is applied in powder form to elements of high tensile strength and the said elements are then pulled through a heated die. The shell material may be applied in powder form to the already shaped filament and the said filament may then be pulled through another heated die. A soluble granular substance may be mixed with the material located in each case on the filament exterior before the application and after pulling through the heated die, and the said substance may be washed out of the filament exterior with a solvent.

Of the two materials combined in the composite material, new functions can be imparted to the support in particular by a special preparation of the constituents, which further broadens the function of the support substance during use of the endoprosthesis in the human or animal body through the contribution of these support materials to the flexural rigidity of the filaments. By this functional vehicle made newly attainable by the invention, the endoprosthesis can now itself assume the tasks which occur regularly in association with its use, but which were accomplished previously only with many complications, with consumption of time, and with stress for the patient by measures independent of the endoprosthesis. The endoprosthesis can now perform certain functions automatically and self-sufficiently during its use in the vessel, even without special external control. By the provision of a multipurpose support the treatment with the endoprosthesis is overall more effective and ultimately has a lower total expenditure. The stressing of the patient with x-rays, with contrast medium or with medications, and also with traumatic interventions can be considerably reduced. Through the selective use of measures at the site of need, the chances of successful treatment with the endoprosthesis become greater so that the use of the composite materials for the fabrication of endoprostheses can now be accepted as a whole. At the same time, despite the additional functions, the high flexural rigidity of a normal composite filament can be easily retained. The support in the composite, different from the elements of high tensile strength, must itself transfer no tensile forces. The flexural rigidity is essentially achieved by a corresponding hardness of the support. It is therefore sufficient for retaining a preset flexural rigidity for the support to exhibit a certain hardness even after the special preparation. This condition is easier to fulfill than, for example, the adherence to a specific tensile strength in the materials technology-based modifications of a starting material.

The filaments of a novel endoprosthesis can be cut such that they are rounded at the ends and have no edges. The risk of the occurrence of thrombogenically acting turbulences is largely removed thereby. They can be fashioned sufficiently stiff with a small diameter so that the endoprosthesis can be inserted very well and nevertheless shows sufficient expansion force.

It is possible by means of the invention to adjust, for example, the surface of the endoprosthesis very accurately to the respective medical requirements without substantially affecting the mechanical properties of the filaments thereby. This applies especially if, by the special preparation of the support, a sized shell surrounding the filament and not substantially altering the tensile strength of the filament is indissolubly anchored in the filament surface of the support. The shell can be very thin so that the compressibility of the endoprosthesis is not adversely affected. The support, the hardness of which greatly determines the stiffness of the filament, can then be selected like the elements of high tensile strength without consideration of the biocompatibility, whereas the shell material can be totally oriented to the last requirement. The support is in this case not only the support for the elements of high tensile strength, but also the support, for example, for a shell selected from medical standpoints. For this task, a mating of materials, support-shell, can be selected in which neither of the paired components must satisfy the requirement of high tensile strength. The method of anchoring the shell on the support can now also be selected totally according to the requirements of safety so that in no case can the shell material detach itself from the filament and enter, for example, the patient's circulation. Therefore all possibilities are open to provide a medically safe base for a broad palette of possible filament shells with respectively highly diverse functions.

An especially intimate and thereby safe combination of the shell material with the support results if both the support and the material of the shell each contain a thermoplastic, and if the thermoplastic of the support is melted onto the filament surface and melted into the thermoplastic of the shell material. The support can then reliably fulfill its task as the base for medically effective filament shells. In special cases, depending on the medical function of the shell and on the selection of the support, the endoprosthesis can be further improved if the shell contains the same thermoplastic as the support.

An advantageous development results if the support or shell material is prepared from a mixture of substances in which a contrast medium is contained. The position of the endoprosthesis can then be observed radiologically at any time during the insertion of the endoprosthesis and also after a prolonged residence time, without the patient having to be given a special contrast medium for this or the patient having to be exposed to an especially high radiation load. This is especially important during use of the endoprosthesis in blood circulation. Contrast media can generally be given as necessary with the endoprosthesis insertion catheter during the insertion of the endoprosthesis, but after a prolonged residence time of the endoprosthesis a special catheter would have to be used again for radiologic monitoring, so that the contrast medium can be brought to the site of the prosthesis in the circulation. The traumatic procedure with the reinserted catheter and the other stresses on the patient are avoided by the new development.

If the material located on the filament exterior is prepared from a mixture of substances in which a medication active in the human or animal body is present, the support then forms not only a bed producing the flexural rigidity for the element of high tensile strength, but it concurrently also forms an implantable medication dosage device. The medication is taken up automatically by the body from the endoprosthesis as soon as the latter is inserted into the body. A specially dosed medication administration from the exterior or another external control is not necessary; the corresponding expenses for the physician and patient are eliminated. In so doing, of primary consideration are medications that are directly associated with the endoprosthesis, which are to prevent, for example, the formation of thrombi at the endoprosthesis. However, still other medications are also conceivable; it is conceivable above all that endoprostheses will be developed which are used only for the purpose of medication release in the human or animal body. In each case, this endoprosthesis permits a precisely dosed use of the medication and above all a very selective use of the medication. Stress on the other body parts by the medication is reduced; the entire amount of the medication remains low, but highly effective doses can be used at the site of need.

It is furthermore advantageous if the material located on the filament exterior during the transition to its solid phase forms an especially large surface on which a coating of the filament is anchored by the special preparation of the support. Many different materials and techniques are suitable as coatings for the filament; for example, sheathing of the entire endoprosthesis is a special application case, the said sheathing which, for example, surrounds a coating of the individual filaments. Biodegradable layers are also suitable as a coating, which release medications, for example, in their breakdown. In regard to coatings for the endoprostheses, however, it is always important that the coating does not separate under any circumstances in an uncontrolled manner, so that no wandering foreign bodies occur in the body. The support with the large surface offers a good base for reliable anchoring of the most diverse coatings. Further processing of the support is not necessary if the large surface forms during the transition of the support to the solid phase.

An especially advantageous design of the endoprosthesis is formed if the material located on the filament exterior forms pores, in which a medication effective in the human or animal body is stored, by the special preparation of the support. Pores can be easily provided in the support or shell material, not designed for tensile strength, without limitations of its suitability as support or shell material. A porous exterior offers the best conditions for taking up defined amounts of liquid substances. The substances must meet no other major requirements other than flowability, so that a broad spectrum of substances is suitable for this purpose. The amount of substance taken up and the release characteristics of the substance can be controlled by the impregnation method, pore size, and number of pores, so that this endoprosthesis is especially suitable for release of medications in the most diverse doses.

Favorable fabrication processes for the endoprostheses result if, for the fabrication of a filament, the support is applied in powder form to the elements of high tensile strength and the said elements are then pulled through a heated die, and if furthermore the shell material is applied in powder form to the filament and the said filament is then pulled through another heated die. This fabrication process is designated as pultrusion and requires relatively little prefabrication. However, it simultaneously permits admixtures in the support available in powder form.

The pores in the carrier or shell material are fabricated advantageously in that a soluble granular substance is added to the material located on the filament exterior before the application to the elements of high tensile strength or to the already shaped filaments, and after pulling through the heated die, the said substance is washed out from the filament exterior with a solvent. In this way pores, which can be especially well controlled in their quality and distribution, can be obtained at very little cost.

In sum, the present invention relates to a body compatible device made of an elongated filament which is substantially uniform in lateral cross-section over its length and is made of multiple fibers having high tensile strength embedded in a polymeric material. The polymeric material may be melted onto the fibers. The filament may have a polymeric elongate case surrounding the filament. The polymeric material embedding the fibers and the polymeric material of the case may be the same polymeric material, and may contain a contrast medium. A case may have a smooth outer surface having a medication applied thereto, and it may have an outer surface with pores which contain a medication. The fibers may be inorganic fibers made of carbon, KELVAR aramid fiber glass, or combinations thereof. The polymeric material embedding the fibers may be made of a polymer selected from the group consisting of polyetherether ketone and polyethersulfone. The device may be made by applying the polymeric material embedding the fibers in powder form to the multiple fibers and then pulling the fibers and powder through a heated die. A case material may be applied in powder form to a preshaped filament and the filament and polymeric case material may then be pulled through a heated die. A soluble granular substance may be applied to the case surface before and after pulling the filament through the heated die, and the soluble granular substance may then be washed off of the case surface with a solvent to thereby reveal pores.

The present invention also relates to a body compatible device made of an elongated filament which is substantially uniform in lateral cross-section over its length and which includes an elongate core and an elongate case surrounding the core; wherein the core is made of multiple fibers having high tensile strength embedded in a polymeric material, and wherein the case is made of a polymeric material having an outer surface. The case may not substantially alter the tensile strength of the core. The polymeric material of the core may be melted onto the fibers and then melt bonded with the polymeric material of the case. The device may be made by applying the polymeric material of the core in powder form to the multiple fibers and then pulling the fibers and powder through a heated die. The case material may be applied in powder form to a preshaped core and the core and polymeric case material may then be pulled through a heated die. A soluble granular substance may be applied to the case surface before and after pulling the filament through the heated die, and the substance may then be washed off of the case surface with a solvent to thereby reveal pores.

The present invention also relates to a body compatible stent made of a tubular latticework of at least one elongated filament substantially uniform in lateral cross-section over its length and made of multiple fibers having high tensile strength embedded in a polymeric material. The polymeric material may be melted onto the fibers.

BRIEF DESCRIPTION OF THE DRAWINGS

Below, the invention will be explained in greater detail on the basis of figures depicting only the embodiments. These figures are provided to illustrate, and not limit, the present invention. Shown in FIG. 1a is a novel endoprosthesis in an expanded state in side view, FIG. 1b the same endoprosthesis in an expanded view in a front view, FIG. 2 the same endoprosthesis in a compressed state in side view, FIG. 3 a cross section through a filament of a novel-endoprosthesis according to the first embodiment, FIG. 4 a cross section through a filament of a novel endoprosthesis according to a second embodiment, FIG. 5 a cross section through a filament of a novel endoprosthesis according to a third embodiment.

An endoprosthesis fashioned as a tubular latticework is shown schematically in FIGS. 1a and 1b, which consists of a series of rigid, elastic filaments 1 bent in a helical line. They form two groups with an opposite sense of rotation of n elements in each case, whereby the filaments in one group are equally distributed over the perimeter so that two neighboring filaments are twisted against each other by $(360/n)°$. The value of n can vary over a broad range; typically it falls between about 8 and 20. The mutually crossing filaments in both groups are interwoven in that each filament crosses that of the other group alternately inwardly and outwardly. The endoprosthesis thereby obtains a solid structure also withstanding larger mechanical loads.

Figure 1A:
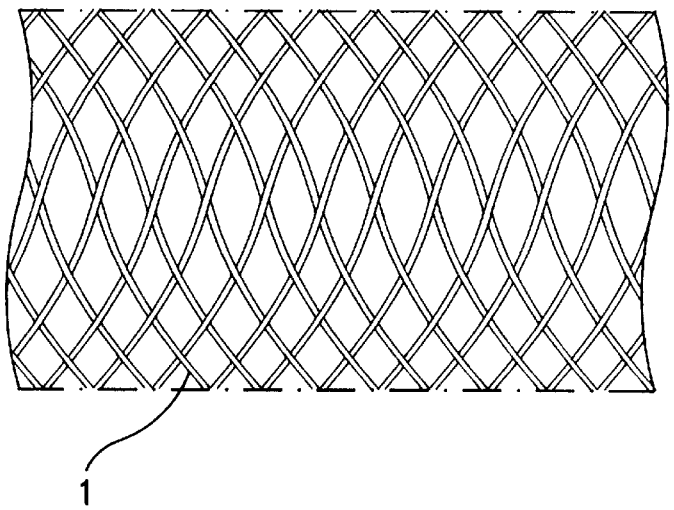
Figure 1B:
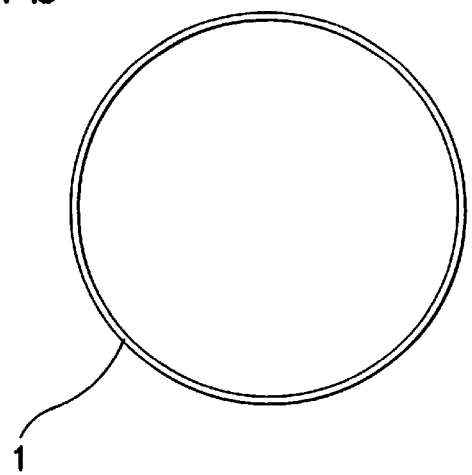
Figure 2:
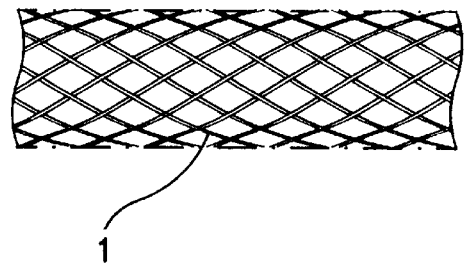

At the same time, the endoprosthesis is readily compressible however. Under the effect of radially, internally directed forces, it is pressed together and stretched, as shown in FIG. 2, whereby the lead of the filament increases, without the structure being altered by this. In this form, the endoprosthesis can be relatively easily introduced, for example, in a shell by means of a catheter. The shell can then be removed, whereupon the endoprosthesis expands and anchors itself securely in the vessel.

Figure 3:
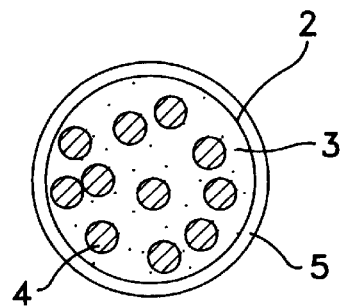
Figure 4:
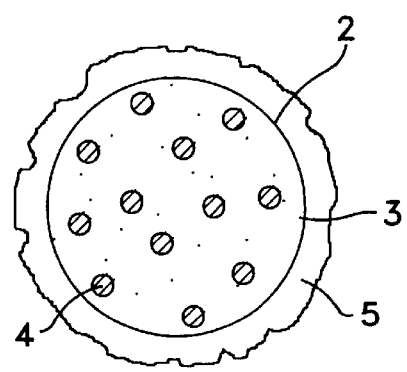
Figure 5:
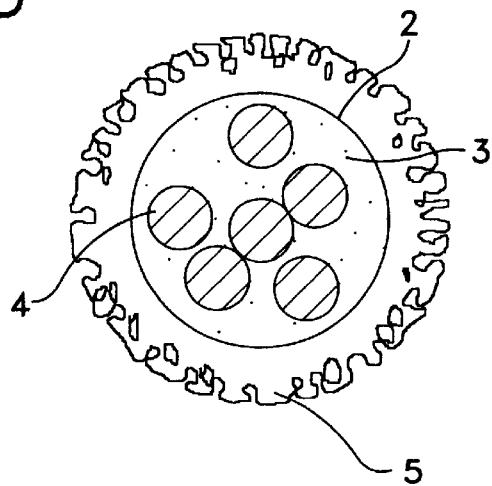

As depicted in FIGS. 3–5, each filament 1 consists of a composite material 2, which, embedded in a support 3 made of plastic, contains reinforcement fibers 4 with a high tensile strength running along the entire length of the filament 1, the said fibers 4 are grouped side by side and preferably distributed somewhat uniformly over the cross-sectional area of the composite material 2. The stiffness of the filament 1 can be adjusted as needed over a broad range by the hardness of the support 3 and by the material and primarily by the thickness of the reinforcement fibers 4. Thus, with the same materials, the filament in FIG. 3 has an average stiffness, that in FIG. 4 low stiffness, and that in FIG. 5 high stiffness. The mechanical properties of the filament 1 can also be selectively influenced by the guidance of the reinforcement fibers 4—intertwining or parallel. The diameters of the filaments generally range from 0.05 to 0.25 mm. Due to the depicted structure, sufficient stiffnesses can be achieved even with small diameters.

Suitable as reinforcement fibers 4 are primarily inorganic fibers, especially, carbon, Kevlar aramid fiber, and glass fibers. Carbon fibers have the advantage of good biocompatibility so that it is not absolutely necessary to assure total sheathing of the said fibers; glass or KEVLAR aramid fiber in contrast must be totally enclosed by biocompatible material.

Complete coating of the reinforcement fibers 4 can be assured by the support 3, which preferably is a high-strength, if possible, thermoplastic. Especially suitable are polyetherether ketone (PEEK) and polyethersulfone (PS).

It is however advantageous to provide filament 1 in each case with an additional shell 5 made of plastic. If the latter is biocompatible, therefore perhaps PEEK or PS, it can be substantially equivalent to support 3, but can have different admixtures and a specially treated surface.

Thus the filament in FIG. 3 exhibits a smooth shell 5, whereas that of the filament in FIG. 4 is roughened. The shell 5 of the filament per FIG. 5, in contrast, has a porous external layer, which is highly suitable for the uptake of medications or other active ingredients, with which it is impregnated before implantation and which it releases after implantation perhaps into the blood stream or surrounding tissue. The rate of release can be adjusted by the suitable selection of the pore size. It is also possible to add the active ingredients directly to the shell material, the said ingredients which are then released only very slowly. In particular, a contrast medium such as bismuth zinc carbonate can be mixed with it—or also with the support—so that the position of the endoprosthesis in the body can be easily monitored.

The pores can be produced in that a soluble granular substance is mixed with the shell material before the latter is applied to the composite material 2 for the fabrication of the shell 5, and after fabrication of the shell 5 the filament is placed in a suitable solvent and the granules are washed out. Salt, for example, can be used as the granular substance, and water as the solvent.

The composite material 2 can be produced in that the reinforcement fibers 4 are sprinkled with the support in powder form and then pulled through a heated die, i.e., pultruded, so that the support becomes viscous and fills the space between the reinforcement fibers 4 and sheaths the said fibers. The shell 5 can then be applied in the same manner in that the composite material 2 is sprinkled with the shell material in powder form (if the shell 5 is to be porous, it can be combined with a soluble granular substance as explained above) and pulled through a second heated die.

I claim:

1. An endoprosthesis for use in vessels of the human or animal body, comprising each of said filaments including a tubular latticework made of flexurally rigid elastic filaments, each of said filaments including a core element of high tensile strength and a shell which surrounds the core element and does not substantially alter the tensile strength of the filament, the shell being designed to receive active substances, wherein the core element consists of a composite material, the composite material being made up of a plurality of high tensile strength, elements which, for the purpose of achieving a high flexural rigidity of the filament, are sheathed by a support material of low tensile strength, and the shell is anchored unreleasably on the support material.

2. The endoprosthesis according to claim 1 wherein both the support material and the shell each comprise a thermoplastic, and the thermoplastic of the support material is melted and fused together with the thermoplastic of the shell material.

3. The endoprosthesis according to claim 2 wherein the shell contains the same thermoplastic as the support material.

4. The endoprosthesis according to claim 1 wherein the support or the shell material is prepared from a mixture of substances which contain a contrast medium.

5. The endoprosthesis according to claim 1 wherein material located on the filament exterior and comprising the shell is prepared from a mixture of substances, which contain a medication effective in a human or animal body.

6. The endoprosthesis according to claim 1 wherein the support material has a surface on which the shell is anchored.

7. The endoprosthesis according to claim 1 wherein material located on the filament exterior and comprising the shell has pores in which a medication effective in the human or animal body is stored.

8. The endoprosthesis of claim 1 wherein the shell is porous and contains a medically active substance in its pores.

9. A body compatible stent comprising at least two interwoven sets of elongate, resilient elements substantially uniform in lateral cross-section over their lengths and forming a tubular latticework which is compressible upon radially internally directed forces to a reduced diameter and self-expandable upon release of the radially internally directed forces to an expanded diameter, wherein the elements comprise:

(a) multiple fibers having high tensile strength;
(b) a first thermoplastic material embedding the fibers to form a composite; and
(c) a second thermoplastic material embedding the composite.

10. The stent of claim 9 wherein the fibers comprise inorganic polymeric fibers.

11. The stent of claim 9 wherein the fibers comprise carbon, Kevlar aramide fibers, glass, or combinations thereof.

12. The stent of claim 9 wherein the first thermoplastic material is polyetheretherketone or polyethersulfone.

13. The stent of claim 9 wherein the first and second thermoplastic materials are, the same polymeric materials.

14. The stent of claim 9 wherein the first polymeric material is melted onto the fibers.

15. The stent of claim 9 wherein the first polymeric material and/or the second polymeric material contain a contrast medium.

16. A body compatible stent comprising at least two interwoven sets of elongate, resilient elements substantially uniform in lateral cross-section over their lengths and forming a tubular latticework which is compressible upon radially internally directed forces to a reduced diameter and self-expandable upon release of the radially internally directed forces to an expanded diameter, wherein the elements comprise:

(a) multiple polymeric fibers having high tensile strength;
(b) a first thermoplastic material embedding the fibers to form a composite; and
(c) a second thermoplastic material embedding the composite and forming a porous exposed outermost surface on the elements which includes a medically active material within its pores.

17. The stent of claim 16 wherein the polymeric fibers comprise inorganic fibers.

18. The stent of claim 16 wherein the polymeric fibers are carbon, Kevlar aramide fibers, glass, or combinations thereof.

19. The stent of claim 16 wherein the first thermoplastic material is polyetheretherketone or polyethersulfone.

20. The stent of claim 16 wherein the first and second thermoplastic materials are the same polymeric materials.

21. The stent of claim 16 wherein the first polymeric material is melted onto the fibers.

22. The stent of claim 16 wherein the first polymeric material and/or the second polymeric material contain a contrast medium.

* * * * *